(12) United States Patent
Clayton et al.

(10) Patent No.: US 11,596,563 B2
(45) Date of Patent: Mar. 7, 2023

(54) FIRST AID TRAUMA KIT CASE

(71) Applicants: Joshua Clayton, Hughson, CA (US);
David Thompson, Denair, CA (US);
Phillip Harris, Oakdale, CA (US)

(72) Inventors: Joshua Clayton, Hughson, CA (US);
David Thompson, Denair, CA (US);
Phillip Harris, Oakdale, CA (US)

( * ) Notice: Subject to any disclaimer, the term of this patent is extended or adjusted under 35 U.S.C. 154(b) by 122 days.

(21) Appl. No.: 16/238,499

(22) Filed: Jan. 2, 2019

(65) Prior Publication Data
US 2020/0206046 A1 Jul. 2, 2020

(51) Int. Cl.
*A61F 17/00* (2006.01)
*A61B 50/30* (2016.01)
*A61B 90/92* (2016.01)

(52) U.S. Cl.
CPC ............ *A61F 17/00* (2013.01); *A61B 50/30* (2016.02); *A61B 90/92* (2016.02); *A61B 2050/3008* (2016.02)

(58) Field of Classification Search
CPC .............................. A61B 90/92; A61F 17/00
USPC ...................................................... 206/459.5
See application file for complete search history.

(56) References Cited

U.S. PATENT DOCUMENTS

2011/0072700 A1* 3/2011 Theresa .................... G09F 3/10
40/638
2017/0281291 A1* 10/2017 Garratt ................... A61B 50/31

OTHER PUBLICATIONS

Survival_Emergency_Products.pdf, AliExpress, https://www.aliexpress.com/item/32323305190.html, Survival Car Medical First Aid Kit (with FDA/CE/TGA) SES01—Home/Workplace Kit, 2016 (Year: 2016).*
Amazon.pdf, Galen VanC, https://www.amazon.com/SURVIVAL-Work-Home-First-Aid/dp/B01K7MDRVY/ref=as_li_ss_tl?s=sporting-goods&ie=UTF8&qid=1524756389&sr=1-1-spons&keywords=survival&psc=1&linkCode=sl1&tag=caracal-20&linkId=c206688c77aacab35a0b62334a554e3b, Great Bag, Feb. 28, 2018 (Year: 2018).*

* cited by examiner

*Primary Examiner* — Allan D Stevens

(57) ABSTRACT

A first aid trauma kit case that provides for a means of treating specific trauma injuries related to massive bleeding and tension pneumothorax. An embodiment of the first aid trauma kit case contains as part of its architecture an easily readable format for identifying an injury location and instructions, that are integrated as part of the case, on how to apply certain specific medical devices contained within the case. An embodiment of the case also provides for a color-coded identification system for easy identification of the preferred treatment method for the suffered trauma injury. The design of the integrated instructions and the color-coded system work in tandem to provide for a quick method of identifying and treating specific types of trauma related injuries.

6 Claims, 3 Drawing Sheets

FIRST AID TRAUMA KIT CASE

FIELD OF INVENTION

The present invention is in the field of medical kits and, more particularly, relates to trauma medical kits for the treatment of emergency medicine in emergency situations.

BACKGROUND

In emergency medical situations where a person is exposed to a trauma related injury, such as an active shooter incident where a person has suffered a gunshot wound to the upper torso, a limb or a junctional area such as the hip or shoulder, time is of the essence for treating treatable life-threatening wounds. More often than not, first responders and professional medical care is not close enough to render the proper medical aid in time to save the life of a person afflicted with this type of treatable traumatic injury. Prior art in this crowded field has attempted to address this issue, however, there has been no widespread acceptance or solution to this problem. A plethora of prior art demonstrate numerous medical kits claiming easy to use treatment for trauma related injuries, however, none address the issue that is the need for specific trauma care that is needed in the gap in time that exists, between the time of traumatic injury and treatment by a first responder or professional medical care. For example a trauma injury that severs the femoral artery can result in death in as little as two minutes, the average response for law enforcement to the scene of an active shooter situation ranges from three to five minutes.

A prior art example provides for a trauma medical kit that treats a wide variety of trauma related injuries ranging from treating an eye injury to massive bleeding and includes a multitude of treatment options accompanied by color coordination and an instructional card. In an emergency situation where a person should be focused on life saving trauma care the addition of non-life threating injury treatment packets can be confusing and overwhelming. An eye injury is not a life-threatening injury that should be compared to a femoral artery bleed which is considered a massive bleed and can result in death in as little as two minutes. Furthermore, in a life-threatening situation the inclusion of a multitude of treatment options for a particular type of injury will only cause confusion and ultimately delay life-saving treatment while a lay person who is attempting to render aid attempts to determine which is the most appropriate treatment option. Every delay wastes precious time that literally means the difference between life and death.

In this same prior art, a separate but connected information chart with pictorial representations of particular treatment steps is provided for to accompany the trauma kit and assist users. This is problematic as the chart can be separated from the kit as any type of tether may break. In another prior art example, a medical compartment cover is provided for which can be removed and provides information for use of the medical care kit contents. This has the same separation issue that is the separation of treatment and instructions to apply such treatments. Medical kits are often carried in a variety of ways and are subject to hard use, accordingly any type of instructional card, chart, or information that can be separated from the kit itself presents the problem of separating the instructions from the medical kits and devices they contain. Without instructions a lay person will not be able to effectively render life-saving aid.

Additional prior art and unpublished prior art examples provide for medical treatment packets. This is problematic in that the precious time it takes opening a package can result in an untimely death. Unpublished prior art examples actually contain life saving trauma devices in a vacuum sealed plastic pouch that takes tools to cut into and open. If a person in need does not have a tool to open the package they will die as a result of not being able to access needed medical devices.

SUMMARY

An embodiment of the invention provides for a first aid trauma kit case that is designed to assist a lay person in the treatment of trauma related injury relating to massive bleeding and tension pneumothorax. The case has a first and second concave section that is hingedly connected along a first edge and means for temporarily attaching the first and second sections in the form of a zipper. The exterior of the said first section has a schemed color-coded human figure diagram and the exterior said second section has a plurality of color coded written instructions. The plurality of color coded written instructions describe how to use the medical devices contained within the first aid trauma kit case. When the first aid trauma kit case is opened the schemed color-coded human figure diagram matches with the color coded plurality of written instructions creating a quick, visual and easy to read means of identifying and treating massive bleeding and tension pneumothorax types of trauma injuries. The ease of use of the invention will help fill the gap of time that exists between the occurrence of a traumatic injury and professional medical care.

An embodiment of the invention provides for an interior of said first concave section and an interior of said second concave section to contain color-coded areas on the interior of each side of the concave sections that hold a medical device within the area that correlate with the schemed color-coded human figure diagram located on the exterior of the said first concave section and plurality of color-coded of written instructions located on the exterior of the said second concave section. This provides for easy identification of needed medical devices to treat a specific type of trauma injury. Additionally, an embodiment of the invention includes an interior which contains color-coded elastic straps on the interior of said first concave section and the interior of said second concave section where the color-coded elastic strap hold a medical device in place that correlate with the schemed color-coded human figure diagram located on the exterior of said first concave section and plurality of color-coded written instructions located on the exterior of said second concave section. In still a further embodiment of the invention the first aid trauma kit case contains a tourniquet, occlusive dressing and gauze. By only containing essential life saving medical devices related to trauma injuries related to massive bleeding and tension pneumothorax the invention will be less intimidating and less confusing to a person not possessing advanced medical training.

DETAILED DESCRIPTION OF THE INVENTION

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

An embodiment of the invention provides a first aid trauma kit case that has a plurality of color-coded written instructions, a schemed color-coded human figure diagram, a color-coded interior and color-coded interior elastic straps that correlate with each other in a manner that is designed to assist a lay person in the treatment of certain trauma related injuries relating to massive bleeding and tension pneumothorax. The term "color-coded" means a scheme of colors that correlate with one another used as part the invention on the plurality of color-coded written instructions, schemed color-coded human figure diagram, interior concave sections and interior elastic straps. For example, a person who has suffered a traumatic injury such as a gunshot wound to the upper torso can recognize on the schemed color-coded human figure diagram a color in the human figure diagram that matches the location of their injury and then they can easily use that color to identify the relevant instructions on the plurality of color-coded written instructions on what medical device to use and how to apply that specific medical device by matching the color located on the schemed color-coded human figure diagram to the plurality of color-coded written instructions located on the opposite exterior side of the invention. The person can then open the invention and identify by the interior and elastic strap color the medical device contained within the invention that treats their injury, in this example an occlusive dressing. The manner in which the schemed color-coded figure diagram and plurality of color-coded written instructions are integrated into the invention provides for an easily readable format similar to that of a book making it easier for person who has suffered a traumatic injury or is in shock from observing someone who has suffered such an injury to identify, read and understand the needed type of treatment and instructions to apply such treatment. Additionally, by integrating these elements into the case there is no risk of separation of instructions from the case.

Figure 1:
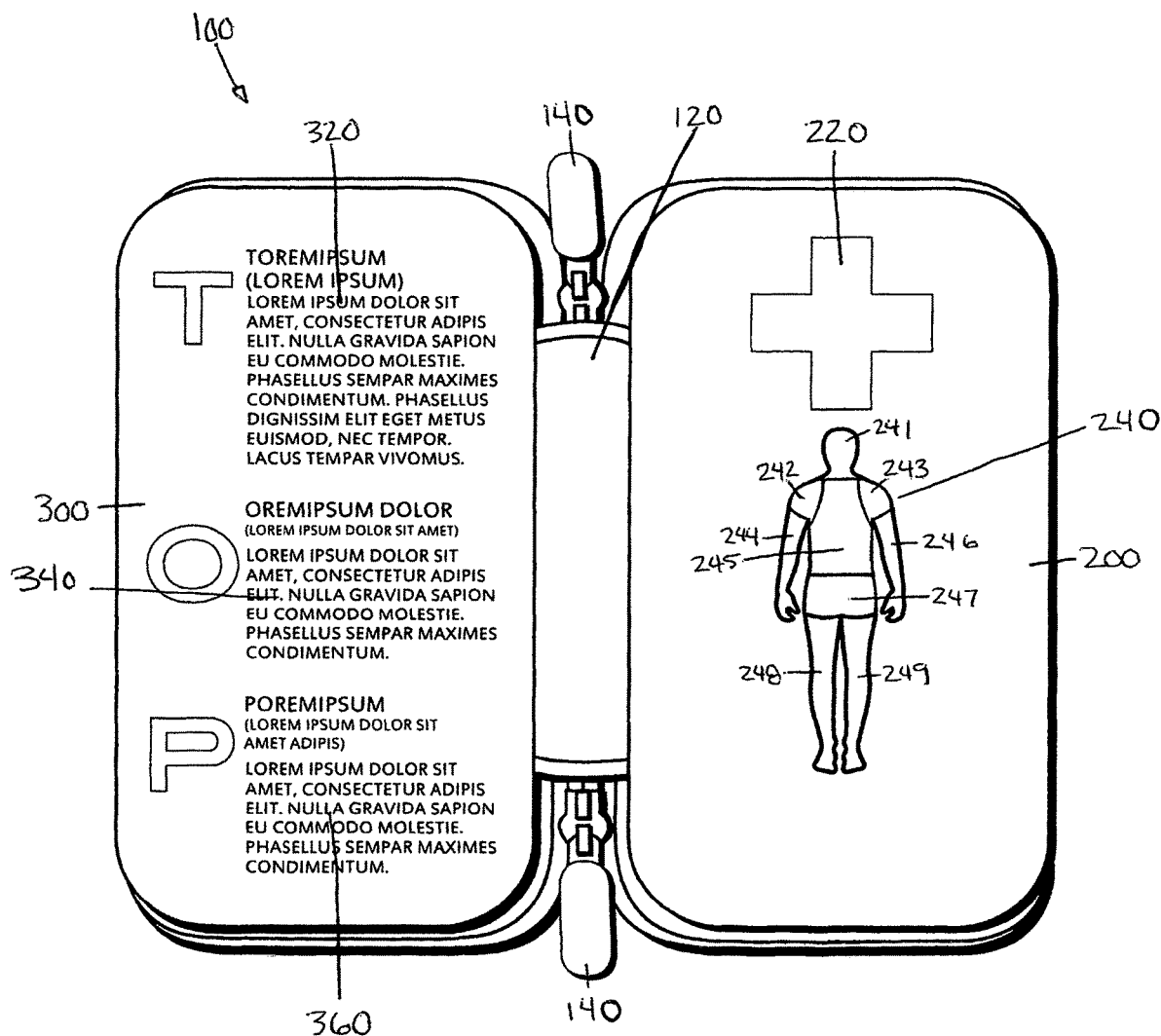
FIG. 1 is a perspective view of the exterior of the present invention showing the first aid trauma kit case in the open position.

FIG. 1. illustrates the exterior of the first aid trauma kit case 100 while in the open position. The first concave section 200 and second concave section 300 are aligned next to one another. The manner in which the schemed color-coded human figure diagram 240 and plurality of color-coded written instructions match save precious time in identifying and treating a life-threatening injury by creating a familiar format. In times of great stress, such as when traumatic injury is suffered, familiarity creates a calming effect. The invention is hingedly connected 120 in a permanent manner on one edge of the first aid trauma kit case 100, while the other edges are able to be connected temporarily, in this embodiment by a zipper 140. The invention can be formed from flexible material, semi-flexible material, rigid material or a combination thereof.

The exterior of the first concave section 200 has a schemed color-coded human figure diagram 240 integrated into its design. In at least one embodiment of the invention the schemed color-coded human figure diagram 240 is divided into nine sections. The head 241, right shoulder 242, left shoulder 243, upper torso 245, right arm 244, left arm 246, hip and pelvic area 247, right leg 248 and left leg 249. It is recognized that these distinguished areas in the schemed color-coded human figure diagram 240 are subject to change depending on the detail of the schemed color-coded human figure diagram 240. The areas that are color-coded are dependent on treatment area locations for massive bleeding and tension pneumothorax. In at least one embodiment of the invention a cross design 220 is located above the schemed color-coded human figure diagram 240.

The exterior of the second concave section 300 has a plurality of color-coded written instructions integrated into its design. In at least one embodiment of the invention instructions for identification and application of three specific medical devices is provided, which are a tourniquet, occlusive sheet and gauze. The color of the instructions will match with colors on the schemed color-coded human figure diagram 240 to identify which medical device is needed to treat a specific injury dependent upon the location of the injury on the body of the person who has suffered the injury. In at least one embodiment the instructions for use of a tourniquet 320 are above the instructions for use of an occlusive dressing 340 is in the middle which is above instructions for use of gauze 360. In an embodiment of the invention the plurality of color-coded written instructions are accompanied by pictorial representations near the written text.

In at least one embodiment of the invention the color located in the right arm 244, left arm 246, right leg 248 and left leg 249 of the schemed human figure diagram 240 will match with color of the instructions for use of a tourniquet 320. The color located in the upper torso 245 of the human figure diagram 240 will match the color of the instructions for use of an occlusive dressing 340. The color located in the right shoulder 242, left shoulder 243 and hip and pelvic area 247 of the human figure diagram 240 will match the color of the instructions for use of gauze 360. The color of the head 241 will not match any color-coded instructions.

In at least one embodiment of the invention the instructions for use of a tourniquet 320, the instructions for use of an occlusive dressing 340 and instructions for use of gauze 360 located on the exterior of the second concave section 300 describe specific instructions for the medical devices contained within the present invention designed to treat massive bleeding and tension pneumothorax. A person trained in the field will recognize that different brands and types of medical devices used to treat massive bleeding and tension pneumothorax will require different instructions. For purposes of this illustration the instructions for use of a tourniquet 320, the instructions for use of an occlusive dressing 340 and instructions for use of gauze 360 are using incoherent text to demonstrate how specific instructions will be displayed.

Figure 2:
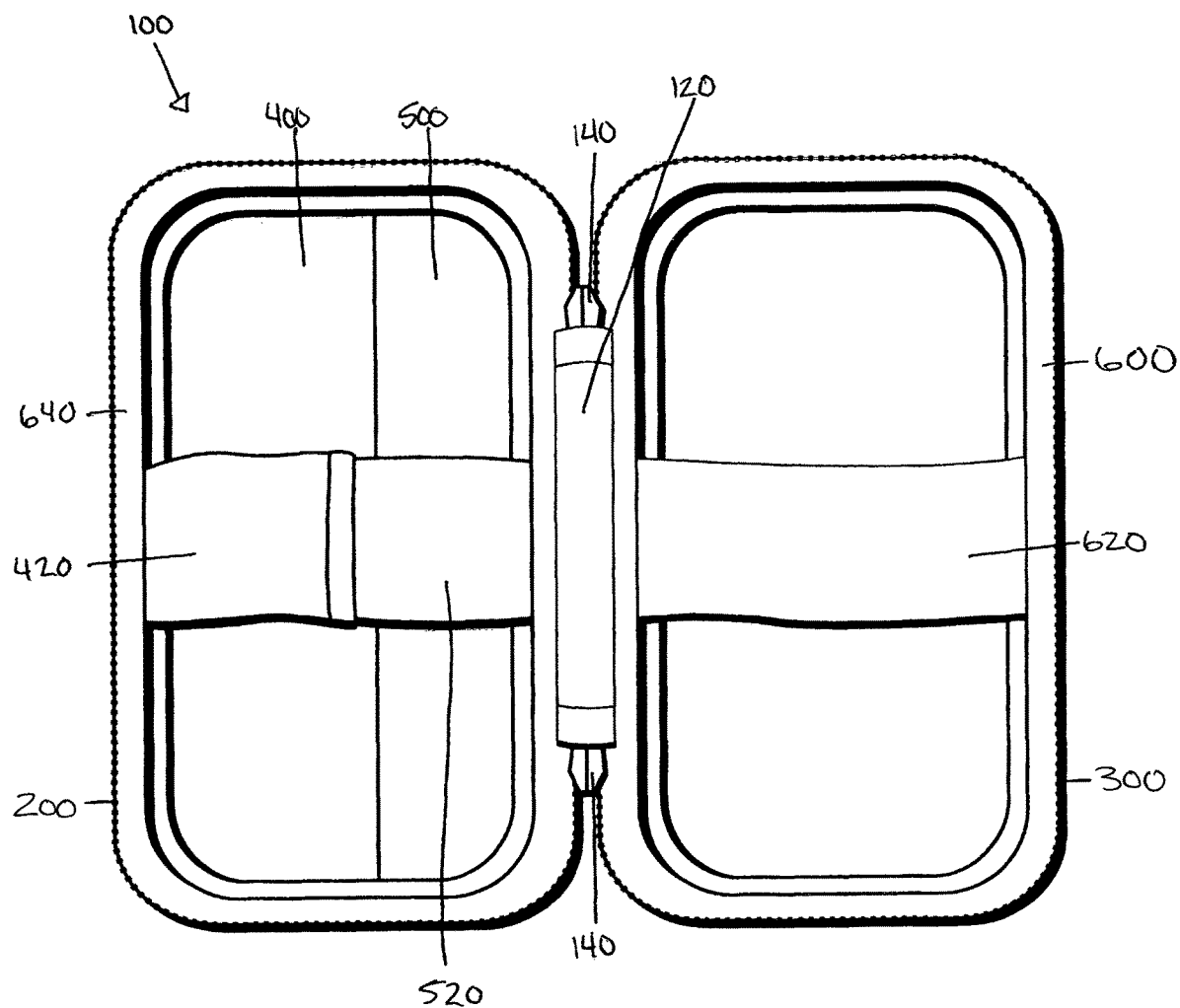
FIG. 2 is a perspective view of the interior of the present invention showing the first aid trauma kit case in the open position.

FIG. 2 illustrates an interior perspective of the present invention in the open position. The first concave section 200 and the second concave section 300 of the first aid trauma kit case 100 is hingedly connected 120, while the other edges of the first aid trauma kit case 100 are affixed with a temporary means, in this embodiment a zipper 140. The configuration of the interior is dependent upon the medical devices contained within it for treatment of massive bleeding and tension pneumothorax. In at least one embodiment of the invention the right interior side 600 is designed to fit and carry an occlusive dressing, while the left interior side 640 is designed to fit and carry a tourniquet and gauze as represented in FIG. 3.

The interior colors of the present invention will be color-coded to identify treatment of specific trauma injuries identified and described on the exterior of the invention by the schemed color-coded human figure diagram and plurality of color-coded written instructions as shown in FIG. 1. The size of the color-coded areas on the interior of each side of the concave sections will be respectively similar to the size of the medical device that is held within that particular area. In at least one embodiment the right interior side 600 color will match the color of the instructions for use of an occlusive dressing 340, the right half portion 500 of the left interior side 640 will match the color of the instructions for use of gauze 360, and the left half portion 400 of the left interior side 640 will match the color of the instructions for use of a tourniquet 320.

The medical devices contained within the present invention are held in place by color-coded elastic straps that match the interior colors they overlap, and exterior colors of the instructions and human figure diagram 240. These elastic straps are permanently affixed to the interior of the invention. In at least one embodiment of the invention the right side elastic strap 620 color will match the color of the instructions for use of an occlusive dressing 340, the elastic strap 520 over the right portion of the left interior side 640 will match the color of the instructions for use of gauze 360, and the elastic strap 420 over the left portion of the left interior side 640 will match the color of the instructions for use of a tourniquet 320.

Figure 3:
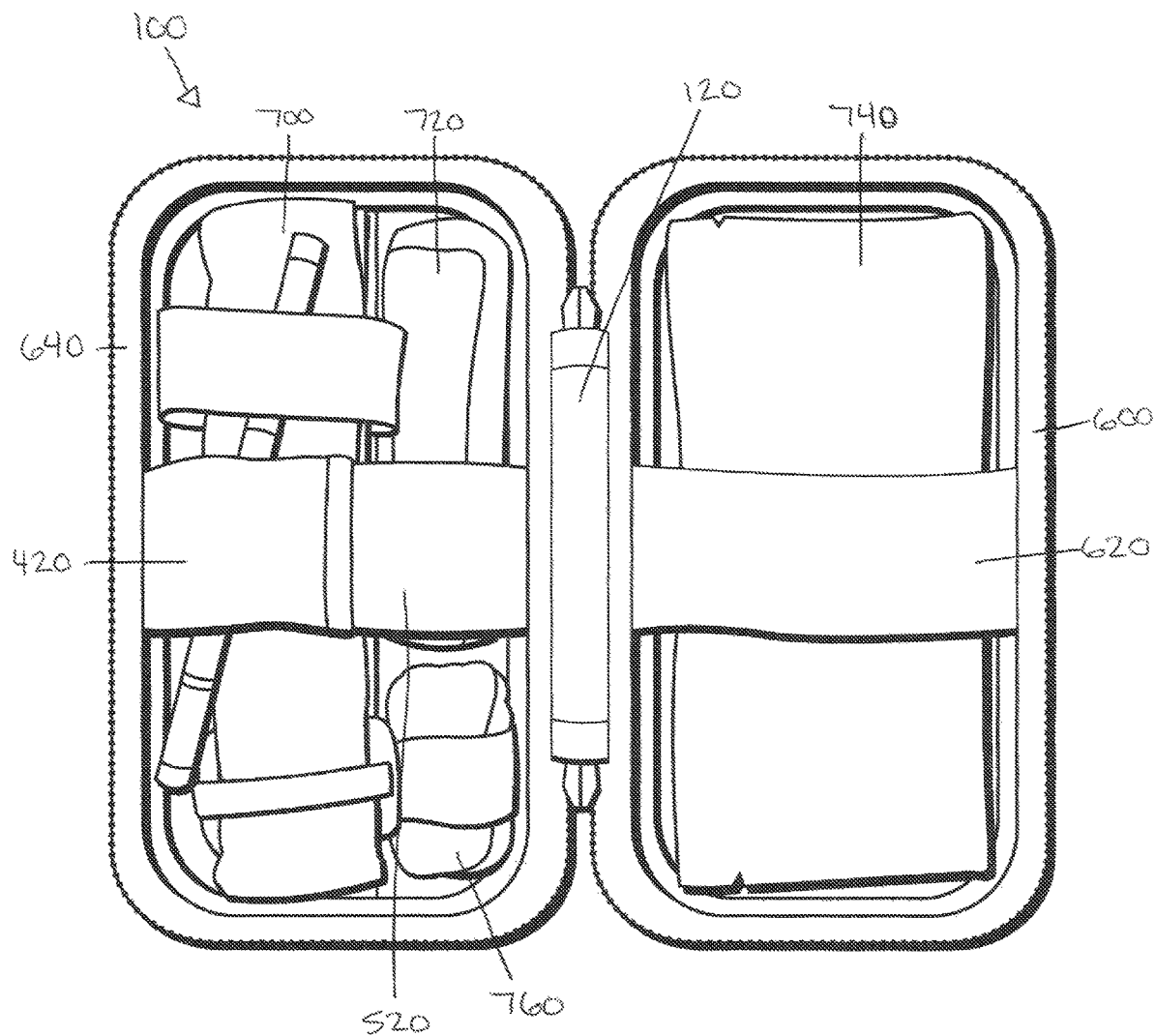
FIG. 3 is a perspective view of the interior of the present invention containing a tourniquet, an occlusive dressing and gauze.

FIG. 3 illustrates an embodiment of the interior perspective of the invention in the open position with the case containing a tourniquet 700, occlusive dressing 740, gauze 720 and plastic gloves 760. The right interior side 600 depicts the right side elastic strap 620 holding in place an occlusive dressing 740 in place. The right elastic strap portion of the left interior side 640 depicts the elastic strap 520 holding in place gauze 720. Below the gauze is a rolled-up pair of plastic gloves 760. The left elastic strap portion of the left interior side 640 depicts the elastic strap 420 holding in place a tourniquet 700. It is recognized that there are alternate configurations for the interior of the invention dependent on the size and design of specific medical devices for the treatment of massive bleeding and tension pneumothorax.

Referring back to FIG. 1 a user of the present invention will be able to locate a color-coding on the schemed color-coded human figure diagram 240 that matches their specific trauma injury, the person will then be able to identify from the color-coding the proper medical device and instructions from matching the plurality of color-coded written instructions located on the second concave section 300 up with the first concave section 200. The person will then be able to use the color-coded interior and elastic straps to easily and quickly identify the proper medical device contained within the first aid trauma kit case 100 and use that medical device to save themselves or another person.

What is claimed is:

1. A first aid trauma kit case, consisting of:
    a case having first concave section and second concave section hingedly connected along a first edge of each section and including a temporary method for attaching the first concave section and the second concave section together along the other edges in the form of a zipper;
    medical devices used for the treatment of massive bleeding or tension pneumothorax limited to a tourniquet, occlusive sheet and gauze;
    a schemed color-coded human figure diagram is located on the exterior of the first concave section;
    a plurality of color-coded written instructions identifying medical treatment for massive bleeding and tension pneumothorax is located on the exterior of the second concave section;
    whereby when said case is opened the schemed color-coded human figure diagram matches with the plurality of color-coded written instructions which create a visual representation for identifying and treating massive bleeding and tension pneumothorax type of trauma injuries.

2. The first aid trauma kit of claim 1 wherein an interior of the first concave section and an interior of the second concave section contain color-coded areas that hold medical devices used for the treatment of massive bleeding or tension pneumothorax limited to the tourniquet, occlusive sheet and gauze, wherein each color-coded area correlates with the schemed color-coded human figure diagram located on the exterior of the first concave section and the plurality of color-coded written instructions located on the exterior of the second concave section;
    wherein the color-coded areas on the interior of the first concave section, the color-coded areas of the interior of the second concave section, schemed color-coded human figure diagram and plurality of color-coded written instructions makes the treatment and application of a medical device readily distinguishable.

3. The first aid trauma kit of claim 1 wherein the interior of the case contains color-coded elastic straps that hold medical devices used for the treatment of massive bleeding or tension pneumothorax limited to the tourniquet, occlusive sheet and gauze, wherein each color-coded elastic strap correlates with the schemed color-coded human figure diagram located on the exterior of the first concave section and the plurality of color-coded written instructions located on the exterior of the second concave section.

4. The first aid trauma kit of claim 1 wherein the interior of the case contains medical devices for the treatment of massive bleeding and tension pneumothorax limited to the tourniquet, occlusive sheet and gauze in designated areas that correlate with the schemed color-coded human figure diagram located on the exterior of the first concave section and the plurality of color-coded written instructions located on the exterior of the second concave section.

5. A first aid trauma kit case, consisting of:
    a case having first concave section and second concave section hingedly connected along a first edge of each section and including a temporary method for attaching the first concave section and the second concave section together along the other edges in the form of a zipper;
    a schemed color-coded human figure diagram is located on the exterior of the first concave section;
    a plurality of color-coded written instructions identifying medical treatment for massive bleeding and tension pneumothorax is located on the exterior of the second concave section;
    whereby when the case is opened the schemed color-coded human figure diagram matches with the plurality of color-coded written instructions;
    a distinct color-coded area on the interior of the first concave section containing a tourniquet that correlates with the schemed color-coded human figure diagram and plurality of color-coded written instructions;

a distinct color-coded area on the interior of the interior of the second concave section containing a occlusive sheet that correlates with the schemed color-coded human figure diagram and plurality of color-coded written instructions;

a distinct color-coded area on the first interior concave section containing gauze that correlates with the schemed color-coded human figure diagram and plurality of color-coded written instructions;

wherein the matching schemed color-coded human figure diagram, plurality of color-coded written instructions, the distinct color-coded areas of the interior of the first concave section and the distinct color-coded area of the interior of the second concave section makes the treatment and application of a medical device readily distinguishable.

6. The first aid trauma kit of claim 5 wherein the interior of the first concave section and the interior of the second concave section contains distinct color-coded elastic straps that respectively hold the tourniquet, occlusive sheet and gauze, wherein each distinct color-coded elastic strap correlates with the schemed color-coded human figure diagram and the plurality of color-coded written instructions.

* * * * *